United States Patent [19]
Reed et al.

[11] Patent Number: 5,942,403
[45] Date of Patent: *Aug. 24, 1999

[54] **COMPOUNDS AND METHODS FOR THE DETECTION OF *T. CRUZI* INFECTION**

[75] Inventors: Steven G. Reed, Bellevue; Raymond Houghton, Bothell; Yasir A. W. Skeiky, Seattle, all of Wash.

[73] Assignee: Corixa Corporation, Seattle, Wash.

[ * ] Notice: This patent is subject to a terminal disclaimer.

[21] Appl. No.: 08/929,414

[22] Filed: Sep. 15, 1997

Related U.S. Application Data

[63] Continuation-in-part of application No. 08/403,379, Mar. 14, 1995, Pat. No. 5,756,662.

[51] Int. Cl.$^6$ .......................... G01N 33/53; A61K 38/00; C07K 2/00; C07K 5/00
[52] U.S. Cl. .......................... 435/7.22; 514/14; 530/300; 530/326
[58] Field of Search .................................... 530/300, 326; 435/7.22, 320.1, 325; 514/14; 536/23.1, 23.4

[56] References Cited

U.S. PATENT DOCUMENTS

| | | | |
|---|---|---|---|
| 4,870,006 | 9/1989 | Dragon et al. | 435/7 |
| 5,304,371 | 4/1994 | Reed | 424/88 |
| 5,756,662 | 5/1998 | Reed | 530/300 |

FOREIGN PATENT DOCUMENTS

| | | |
|---|---|---|
| WO 90/02564 | 3/1990 | WIPO . |
| WO 92/09895 | 6/1992 | WIPO . |
| WO 93/16199 | 8/1993 | WIPO . |
| WO 94/01776 | 1/1994 | WIPO . |

OTHER PUBLICATIONS

Burns et al. "Identification and Synthesis of a major conserved antigenic epitope of Trypanosoma cruzi" Proc. Nat. Acad. Sci. USA; vol. 89, pp. 1239–1243, Feb. 1992.

Hoft et al. "Trypanosoma cruzi Expresses Diverse Repetitive Protein Antigens" Infect. Immunit.; vol. 57, pp. 1959–1967, Jul. 1989.

Buschiazzo et al., "Sequence of the gene for a *Trypanosoma cruzi* protein antigenic during the chronic phase of human Chagas disease," *Molecular and Biochemical Parasitology* 54: 125–128, 1992.

Campetella et al., "A Superfamily of *Trypanosoma cruzi* Antigens," *Parasitology Today* 8 (11): 378–381, 1992.

Frasch and Reyes, "Diagnosis of Chagas Disease Using Recombinant DNA Technology," *Parasitology Today* 6(4): 137–139, 1990.

Frasch et al., "Comparison of Genes Encoding *Trypanosoma cruzi* Antigens," *Parasitology Today* 7(6): 148–151, 1991.

Hoft et al., "*Trypanosoma cruzi* Expresses Diverse Repetitive Protein Antigens," *Infection and Immunity* 57(7): 1959–1967, 1989.

Ibanez et al., "Multiple *Trypanosoma cruzi* antigens containing tandemly repeated amino acid sequence motifs," *Molecular and Biochemical Parasitology* 30: 27–34, 1988.

Peralta et al., "Serodiagnosis of Chags' Disease by Enzyme–Linked Immunosorbent Assay Using Two Synthetic Peptides as Antigens," *Journal of Clinical Microbiology* 32(4): 971–974, 1994.

Skeiky et al., "Antigens Shared by *Leishmania* Species and *Trypanosoma cruzi*: Immunological Comparison of the Acidic Ribosomal P0 Proteins," *Infection and Immunity* 62(5): 1643–1651, 1994.

Skeiky et al., "Cloning and Expression of *Trypanosoma cruzi* Ribosomal Protein P0 and Epitope Analysis of Anti–P0 Autoantibodies in Chagas' Disease Patients," *J. Exp. Med.* 176: 201–211, 1992.

Skeiky et al., "*Trypanosoma cruzi* Acidic Ribosomal P Protein Gene Family," *Journal of Immunology* 151(10): 5504–5515, 1993.

Vergara et al., "Assay for Detection of *Trypanosoma cruzi* Antibodies in Human Sera Based on Reaction with Synthetic Peptides," *Journal of Clinical Microbiology* 29(9): 2034–2037, 1991.

*Primary Examiner*—Lisa B. Arthur
*Assistant Examiner*—Jehanne Souaya
*Attorney, Agent, or Firm*—Seed and Berry LLP

[57] ABSTRACT

Compounds and methods for diagnosing *Trypanosoma cruzi* infection, or for screening for *T. cruzi* or Leishmania infection, are disclosed. The disclosed compounds are polypeptides, or antibodies thereto, that contain one or more antigenic epitopes of *T. cruzi* proteins. The compounds are useful in a variety of immunoassays for detecting *T. cruzi* infection. The polypeptide compounds are further useful in vaccines and pharmaceutical compositions for preventing Chagas' disease in individuals exposed to *T. cruzi*.

19 Claims, 9 Drawing Sheets

```
GAGGGTACCC GCGAAGCCCG CATGCCGAGC AAGGAGCTGT GGATGCGCCG TCTGCGCATT    60
CTCCGCCGCC TGCTGCGCAA GTACCGCGAG GAGAAGAAGA TTGACCGCCA CATCTACCGC   120
GAGCTGTACG TGAAGGCGAA GGGGAACGTG TTTCGCAACA AGCGTAACCT CATGGAGCAC   180
ATCCACAAGG TGAAGAACGA GAAGAAGAAG GAAAGGCAGC TGGCTGAGCA GCTCGCGGCG   240
AAGCGCCTGA AGGATGAGCA GCACCGTCAC AAGGCCCGCA AGCAGGAGCT GCGTAAGCGC   300
GAGAAGGACC GCGAGCGTGC GCGTCGCGAA GATGCTGCCG CTGCCGCCGC CGCGAAGCAG   360
AAAGCTGCTG CGAAGAAGGC CGCTGCTCCC TCTGGCAAGA AGTCCGCGAA GGCTGCTATT   420
GCACCTGCGA AGGCCGCTGC TGCACCTGCG AAGGCCGCTG CTGCACCTGC GAAGGCTGCT   480
GCTGCACCTG CGAAGGCCGC TGCTGCACCT GCGAAGGCTG CTGCTGCACC TGCGAAGGCT   540
GCTACTGCAC CTGCGAAGGC TGCTGCTGCA CCTGCCAAGA CCGCTGCTGC ACCTGCGAAG   600
GCTGCTGCAC CTGCGAAGGC CGCTGCTGCA CCTGCGAAGG CCGCTACTGC ACCTGCGAAG   660
GCTGCTGCTG CACCTGCGAA GGCCGCTACT GCACCTGCGA AGGCTGCTAC TGCACCTGCG   720
AAGGCTGCTG CTGCACCTGC GAAGGCCGCT ACTGCACCCG TTGGAAAGAA GGCTGGTGGC   780
AAGAAG                                                              786
```

*Fig. 1*

Glu Gly Thr Arg Glu Ala Arg Met Pro Ser Lys Glu Leu Trp Met Arg
 1                   5                    10                  15
Arg Leu Arg Ile Leu Arg Arg Leu Leu Arg Lys Tyr Arg Glu Glu Lys
             20                  25                  30
Lys Ile Asp Arg His Ile Tyr Arg Glu Leu Tyr Val Lys Ala Lys Gly
         35                  40                  45
Asn Val Phe Arg Asn Lys Arg Asn Leu Met Glu His Ile His Lys Val
     50                  55                  60
Lys Asn Glu Lys Lys Lys Glu Arg Gln Leu Ala Glu Gln Leu Ala Ala
 65                  70                  75                  80
Lys Arg Leu Lys Asp Glu Gln His Arg His Lys Ala Arg Lys Gln Glu
             85                  90                  95
Leu Arg Lys Arg Glu Lys Asp Arg Glu Arg Ala Arg Arg Glu Asp Ala
             100                 105                 110
Ala Ala Ala Ala Ala Ala Lys Gln Lys Ala Ala Ala Lys Lys Ala Ala
         115                 120                 125
Ala Pro Ser Gly Lys Lys Ser Ala Lys Ala Ala Ile Ala Pro Ala Lys
 130                 135                 140
Ala Ala Ala Ala Pro Ala Lys Ala Ala Ala Ala Pro Ala Lys Ala Ala
145                 150                 155                 160
Ala Ala Pro Ala Lys Ala Ala Ala Ala Pro Ala Lys Ala Ala Ala Ala
             165                 170                 175
Pro Ala Lys Ala Ala Thr Ala Pro Ala Lys Ala Ala Ala Ala Pro Ala
             180                 185                 190
Lys Thr Ala Ala Ala Pro Ala Lys Ala Ala Ala Pro Ala Lys Ala Ala
         195                 200                 205
Ala Ala Pro Ala Lys Ala Ala Thr Ala Pro Ala Lys Ala Ala Ala Ala
         210                 215                 220
Pro Ala Lys Ala Ala Thr Ala Pro Ala Lys Ala Ala Thr Ala Pro Ala
225                 230                 235                 240
Lys Ala Ala Ala Ala Pro Ala Lys Ala Ala Thr Ala Pro Val Gly Lys
                 245                 250                 255
Lys Ala Gly Gly Lys Lys
             260

*Fig. 2*

Lys Ala Ala Ile Ala Pro Ala Lys Ala Ala Ala Ala Pro Ala Lys Ala
1               5                   10                  15
Ala Thr Ala Pro Ala
        20

*Fig. 3*

```
GAATTCA GCA GAG CCC AAA CCA GCG GAG CCG AAG TCA GCA GAG CCT AAA         49
        Ala Glu Pro Lys Pro Ala Glu Pro Lys Ser Ala Glu Pro Lys
         1               5                       10
CCA GCG GAG CCG AAA TCG GCA GAG CCC AAA CCA GCG GAG CCG AAA TCG         97
Pro Ala Glu Pro Lys Ser Ala Glu Pro Lys Pro Ala Glu Pro Lys Ser
 15              20                  25                      30
GCA GAG CCC AAA CCA GCG GAG CCG AAA TCA GCG GGG CCT AAA CCA GCG         145
Ala Glu Pro Lys Pro Ala Glu Pro Lys Ser Ala Gly Pro Lys Pro Ala
             35                  40                  45
GAG CCG AAG TCA GCG GAG CCT AAA CCA GCG GAG CCG AAA TCA GCA GAG         193
Glu Pro Lys Ser Ala Glu Pro Lys Pro Ala Glu Pro Lys Ser Ala Glu
             50                  55                  60
CCC AAA CCA GCG GAG CCG AAA TCG GCA GAG CCC AAA CCA GCG GAG CCG         241
Pro Lys Pro Ala Glu Pro Lys Ser Ala Glu Pro Lys Pro Ala Glu Pro
         65                  70                  75
AAG TCA GCA GAG CCC AAA CCA GCG GAG TCG AAG TCA GCA GAG CCT AAA         289
Lys Ser Ala Glu Pro Lys Pro Ala Glu Ser Lys Ser Ala Glu Pro Lys
         80                  85                  90
CCA GCG GAG CCG AAA TCA GCA GAG CCC AAA CCA GCG GAG TCG AAG TCA         337
Pro Ala Glu Pro Lys Ser Ala Glu Pro Lys Pro Ala Glu Ser Lys Ser
 95                 100                 105                 110
GCA GAG CCC AAA CCA GCG GAG CCG AAG TCA GCA GAG CCC AAA CCA GCG         385
Ala Glu Pro Lys Pro Ala Glu Pro Lys Ser Ala Glu Pro Lys Pro Ala
                115                 120                 125
GAG CCG AAG TCA GCA GAG CCC AAA CCA GCG GAG CCG AAA TCA GCG GAG         433
Glu Pro Lys Ser Ala Glu Pro Lys Pro Ala Glu Pro Lys Ser Ala Glu
            130                 135                 140
CCC AAA CCA GCG GAG CCG AAA TCA GCA GAG CCC AAA CCA GCG GAG TCG         481
Pro Lys Pro Ala Glu Pro Lys Ser Ala Glu Pro Lys Pro Ala Glu Ser
            145                 150                 155
AAA TCA GCG GGG CCT AAA CCA GCG GAG CCG AAG TCA GCG GAG CCA AAA         529
Lys Ser Ala Gly Pro Lys Pro Ala Glu Pro Lys Ser Ala Glu Pro Lys
        160                 165                 170
CCA GCG GAG CCG AAA TCA GCG GAG CCA AAA CCA GCG GAG CCG AAA TCG         577
Pro Ala Glu Pro Lys Ser Ala Glu Pro Lys Pro Ala Glu Pro Lys Ser
175                 180                 185                 190
GCA GAG CCC AAA CCA GCG GAG CCG AAG TCA GCA GAG CCA AAA CCA GCG         625
Ala Glu Pro Lys Pro Ala Glu Pro Lys Ser Ala Glu Pro Lys Pro Ala
                195                 200                 205
GAG CCGAATTC                                                            636
Glu
```

*Fig. 4*

Gly Asp Lys Pro Ser Pro Phe Gly Gln Ala Ala Ala Gly Asp Lys Pro
1              5                   10                  15
Ser Pro Phe Gly Gln Ala
            20

*Fig. 5*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
          (A) LENGTH: 262 amino acids
          (B) TYPE: amino acid
          (D) TOPOLOGY: linear (ii) MOLECULE TYPE: protein (xi) SEQUENCE DESCRIPTION: SEQ ID NO:1:

```
Glu Gly Thr Arg Glu Ala Arg Met Pro Ser Lys Glu Leu Trp Met Arg
 1               5                  10                  15

Arg Leu Arg Ile Leu Arg Arg Leu Leu Arg Lys Tyr Arg Glu Glu Lys
            20                  25                  30

Lys Ile Asp Arg His Ile Tyr Arg Glu Leu Tyr Val Lys Ala Lys Gly
            35                  40                  45

Asn Val Phe Arg Asn Lys Arg Asn Leu Met Glu His Ile His Lys Val
        50                  55                  60

Lys Asn Glu Lys Lys Lys Glu Arg Gln Leu Ala Glu Gln Leu Ala Ala
65                  70                  75                  80

Lys Arg Leu Lys Asp Glu Gln His Arg His Lys Ala Arg Lys Gln Glu
            85                  90                  95

Leu Arg Lys Arg Glu Lys Asp Arg Glu Arg Ala Arg Arg Glu Asp Ala
            100                 105                 110

Ala Ala Ala Ala Ala Lys Gln Lys Ala Ala Lys Lys Ala Ala
            115                 120                 125

Ala Pro Ser Gly Lys Lys Ser Ala Lys Ala Ile Ala Pro Ala Lys
            130                 135                 140

Ala Ala Ala Ala Pro Ala Lys Ala Ala Ala Pro Ala Lys Ala Ala
145                 150                 155                 160

Ala Ala Pro Ala Lys Ala Ala Ala Pro Ala Lys Ala Ala Ala Ala
            165                 170                 175

Pro Ala Lys Ala Ala Thr Ala Pro Ala Lys Ala Ala Ala Ala Pro Ala
                180                 185                 190

Lys Thr Ala Ala Ala Pro Ala Lys Ala Ala Pro Ala Lys Ala Ala
            195                 200                 205

Ala Ala Pro Ala Lys Ala Ala Thr Ala Pro Ala Lys Ala Ala Ala Ala
            210                 215                 220

Pro Ala Lys Ala Ala Thr Ala Pro Ala Lys Ala Ala Thr Ala Pro Ala
225                 230                 235                 240

Lys Ala Ala Ala Pro Ala Lys Ala Ala Thr Ala Pro Val Gly Lys
                245                 250                 255

Lys Ala Gly Gly Lys Lys
            260

(2) INFORMATION FOR SEQ ID NO:2:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO:2:

GAGGGTACCC GCGAAGCCCG CATGCCGAGC AAGGAGCTGT GGATGCGCCG TCTGCGCATT        60

CTCCGCCGCC TGCTGCGCAA GTACCGCGAG GAGAAGAAGA TTGACCGCCA CATCTACCGC       120

GAGCTGTACG TGAAGGCGAA GGGGAACGTG TTTCGCAACA AGCGTAACCT CATGGAGCAC       180

ATCCACAAGG TGAAGAACGA GAAGAAGAAG GAAAGGCAGC TGGCTGAGCA GCTCGCGGCG       240

AAGCGCCTGA AGGATGAGCA GCACCGTCAC AAGGCCCGCA AGCAGGAGCT GCGTAAGCGC       300

GAGAAGGACC GCGAGCGTGC GCGTCGCGAA GATGCTGCCG CTGCCGCCGC CGCGAAGCAG       360

AAAGCTGCTG CGAAGAAGGC CGCTGCTCCC TCTGGCAAGA AGTCCGCGAA GGCTGCTATT       420

GCACCTGCGA AGGCCGCTGC TGCACCTGCG AAGGCCGCTG CTGCACCTGC GAAGGCTGCT       480

GCTGCACCTG CGAAGGCCGC TGCTGCACCT GCGAAGGCTG CTGCTGCACC TGCGAAGGCT       540
```

```
GCTACTGCAC CTGCGAAGGC TGCTGCTGCA CCTGCCAAGA CCGCTGCTGC ACCTGCGAAG         600

GCTGCTGCAC CTGCGAAGGC CGCTGCTGCA CCTGCGAAGG CCGCTACTGC ACCTGCGAAG         660

GCTGCTGCTG CACCTGCGAA GGCCGCTACT GCACCTGCGA AGGCTGCTAC TGCACCTGCG         720

AAGGCTGCTG CTGCACCTGC GAAGGCCGCT ACTGCACCCG TTGGAAAGAA GGCTGGTGGC         780

AAGAAG                                                                   786

(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:3:

Lys Ala Ala Ile Ala Pro Ala Lys Ala Ala Ala Pro Ala Lys Ala
1               5                   10                  15

Ala Thr Ala Pro Ala
            20

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:4:

Gly Asp Lys Pro Ser Pro Phe Gly Gln Ala Ala Ala Gly Asp Lys Pro
1               5                   10                  15

Ser Pro Phe Gly Gln Ala
            20

(2) INFORMATION FOR SEQ ID NO:5:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 8..628

(xi) SEQUENCE DESCRIPTION: SEQ ID NO:5:

GAATTCA GCA GAG CCC AAA CCA GCG GAG CCG AAG TCA GCA GAG CCT AAA          49
        Ala Glu Pro Lys Pro Ala Glu Pro Lys Ser Ala Glu Pro Lys
        1               5                   10

CCA GCG GAG CCG AAA TCG GCA GAG CCC AAA CCA GCG GAG CCG AAA TCG          97
Pro Ala Glu Pro Lys Ser Ala Glu Pro Lys Pro Ala Glu Pro Lys Ser
15                  20                  25                  30

GCA GAG CCC AAA CCA GCG GAG CCG AAA TCA GCG GGG CCT AAA CCA GCG         145
Ala Glu Pro Lys Pro Ala Glu Pro Lys Ser Ala Gly Pro Lys Pro Ala
35                  40                  45

GAG CCG AAG TCA GCG GAG CCT AAA CCA GCG GAG CCG AAA TCA GCA GAG         193
Glu Pro Lys Ser Ala Glu Pro Lys Pro Ala Glu Pro Lys Ser Ala Glu
50                  55                  60

CCC AAA CCA GCG GAG CCG AAA TCG GCA GAG CCC AAA CCA GCG GAG CCG         241
Pro Lys Pro Ala Glu Pro Lys Ser Ala Glu Pro Lys Pro Ala Glu Pro
65                  70                  75

AAG TCA GCA GAG CCC AAA CCA GCG GAG TCG AAG TCA GCA GAG CCT AAA         289
```

-continued

```
Lys Ser Ala Glu Pro Lys Pro Ala Glu Ser Lys Ser Ala Glu Pro Lys
 80                  85                  90

CCA GCG GAG CCG AAA TCA GCA GAG CCC AAA CCA GCG GAG TCG AAG TCA        337
Pro Ala Glu Pro Lys Ser Ala Glu Pro Lys Pro Ala Glu Ser Lys Ser
 95                 100                 105                 110

GCA GAG CCC AAA CCA GCG GAG CCG AAG TCA GCA GAG CCC AAA CCA GCG        385
Ala Glu Pro Lys Pro Ala Glu Pro Lys Ser Ala Glu Pro Lys Pro Ala
115                 120                 125

GAG CCG AAG TCA GCA GAG CCC AAA CCA GCG GAG CCG AAA TCA GCG GAG        433
Glu Pro Lys Ser Ala Glu Pro Lys Pro Ala Glu Pro Lys Ser Ala Glu
        130                 135                 140

CCC AAA CCA GCG GAG CCG AAA TCA GCA GAG CCC AAA CCA GCG GAG TCG        481
Pro Lys Pro Ala Glu Pro Lys Ser Ala Glu Pro Lys Pro Ala Glu Ser
145                 150                 155

AAA TCA GCG GGG CCT AAA CCA GCG GAG CCG AAG TCA GCG GAG CCA AAA        529
Lys Ser Ala Gly Pro Lys Pro Ala Glu Pro Lys Ser Ala Glu Pro Lys
160                 165                 170

CCA GCG GAG CCG AAA TCA GCG GAG CCA AAA CCA GCG GAG CCG AAA TCG        577
Pro Ala Glu Pro Lys Ser Ala Glu Pro Lys Pro Ala Glu Pro Lys Ser
175                 180                 185                 190

GCA GAG CCC AAA CCA GCG GAG CCG AAG TCA GCA GAG CCA AAA CCA GCG        625
Ala Glu Pro Lys Pro Ala Glu Pro Lys Ser Ala Glu Pro Lys Pro Ala
195                 200                 205

GAG CCGAATTC                                                           636
Glu
```

(2) INFORMATION FOR SEQ ID NO:6:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Glu Pro Lys Pro Ala Glu Pro Lys Ser Ala Glu Pro Lys Pro Ala
 1               5                  10                  15

Glu Pro Lys Ser Ala Glu Pro Lys Pro Ala Glu Pro Lys Ser Ala Glu
             20                  25                  30

Pro Lys Pro Ala Glu Pro Lys Ser Ala Gly Pro Lys Pro Ala Glu Pro
         35                  40                  45

Lys Ser Ala Glu Pro Lys Pro Ala Glu Pro Lys Ser Ala Glu Pro Lys
 50                  55                  60

Pro Ala Glu Pro Lys Ser Ala Glu Pro Lys Pro Ala Glu Pro Lys Ser
 65                  70                  75                  80

Ala Glu Pro Lys Pro Ala Glu Ser Lys Ser Ala Glu Pro Lys Pro Ala
                 85                  90                  95

Glu Pro Lys Ser Ala Glu Pro Lys Pro Ala Glu Ser Lys Ser Ala Glu
                100                 105                 110

Pro Lys Pro Ala Glu Pro Lys Ser Ala Glu Pro Lys Pro Ala Glu Pro
            115                 120                 125

Lys Ser Ala Glu Pro Lys Pro Ala Glu Pro Lys Ser Ala Glu Pro Lys
130                 135                 140

Pro Ala Glu Pro Lys Ser Ala Glu Pro Lys Pro Ala Glu Ser Lys Ser
145                 150                 155                 160

Ala Gly Pro Lys Pro Ala Glu Pro Lys Ser Ala Glu Pro Lys Pro Ala
                165                 170                 175

Glu Pro Lys Ser Ala Glu Pro Lys Pro Ala Glu Pro Lys Ser Ala Glu
```

```
                      180                 185                 190
Pro Lys Pro Ala Glu Pro Lys Ser Ala Glu Pro Lys Pro Ala Glu
            195                 200                 205
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:7:

```
Pro Ser Pro Phe Gly Gln Ala Ala Gly Asp Lys
1               5                   10
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:8:

```
Ala Glu Pro Lys Ser Ala Glu Pro Lys Pro Ala Glu Pro Lys Ser
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:9:

```
Ala Glu Pro Lys Pro Ala Glu Pro Lys Ser Ala Glu Pro Lys Pro
1               5                   10                  15
```

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:10:

```
Lys Ala Ala Ile Ala Pro Ala Lys Ala Ala Ala Pro Ala Lys Ala
1               5                   10                  15
Ala Thr Ala Pro Ala
            20
```

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:11:

```
Lys Ala Ala Ala Ala Pro Ala Lys Ala Ala Ala Pro Ala Lys Ala
1               5                   10                  15
Ala Ala Ala Pro Ala
            20
```

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:12:

```
Lys Ala Ala Thr Ala Pro Ala Lys Ala Ala Thr Ala Pro Ala Lys Ala
1               5                  10                  15
Ala Thr Ala Pro Ala
            20
```

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:13:

```
Lys Ala Ala Ile Ala Pro Ala Lys Ala Ala Ile Ala Pro Ala Lys Ala
1               5                  10                  15
Ala Ile Ala Pro Ala
            20
```

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:14:

```
Lys Ala Ala Ala Ala Pro Ala Lys Ala Ala Ala Ala Pro Ala
1               5                  10
```

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:15:

```
Lys Ala Ala Ala Ala Pro Ala Lys Ala Ala Thr Ala Pro Ala
1               5                  10
```

COMPOUNDS AND METHODS FOR THE DETECTION OF T. CRUZI INFECTION

CROSS-REFERENCE TO RELATED APPLICATIONS

This application is a continuation-in-part of U.S. application Ser. No. 08/403,379, filed Mar. 14, 1995, issued May 26, 1998, as U.S. Pat. No. 5,756,662.

TECHNICAL FIELD

The present invention relates generally to the diagnosis of T. cruzi infection and leishmaniasis. The invention is more particularly related to the use of one or more T. cruzi antigenic peptides, or antibodies thereto, in methods and diagnostic kits to screen individuals and blood supplies for the presence of antibodies to T. cruzi. The invention is also directed to vaccine compositions for immunizing an individual to prevent Chagas' disease.

BACKGROUND OF THE INVENTION

Protozoan parasites are a serious health threat in many areas of the world. Trypanosoma cruzi (T. cruzi) is one such parasite that infects millions of individuals, primarily in Central and South America. Infections with this parasite can cause Chagas' disease, which can result in chronic heart disease and a variety of immune system disorders. It is estimated that 18 million people in Latin America are infected with T. cruzi, but there is no definitive treatment for the infection or its clinical manifestations.

The most significant route of transmission in areas where the disease is endemic is through contact with an infected triatomid bug. In other areas, however, blood transfusions are the dominant means of transmission. To inhibit the transmission of T. cruzi in such regions, it is necessary to develop accurate methods for diagnosing T. cruzi infection in individuals and for screening blood supplies. Blood bank screening is particularly important in South America, where 0.1%–62% of samples may be infected and where the parasite is frequently transmitted by blood transfusion. There is also increasing concern that the blood supply in certain U.S. cities may be contaminated with T. cruzi parasites.

The diagnosis of T. cruzi infection has been problematic, since accurate methods for detecting the parasite that are suitable for routine use have been unavailable. During the acute phase of infection, which may last for decades, the infection may remain quiescent and the host may be asymptomatic. As a result, serological tests for T. cruzi infection are the most reliable and the most commonly used.

Such diagnoses are complicated, however, by the complex life cycle of the parasite and the diverse immune responses of the host. The parasite passes through an epimastigote stage in the insect vector and two main stages in the mammalian host. One host stage is present in blood (the trypomastigote stage) and a second stage is intracellular (the amastigote stage). The multiple stages result in a diversity of antigens presented by the parasite during infection. In addition, immune responses to protozoan infection are complex, involving both humoral and cell-mediated responses to the array of parasite antigens.

While detecting antibodies against parasite antigens is the most common and reliable method of diagnosing clinical and subclinical infections, current tests are expensive and difficult. Most serological tests use whole or lysed T. cruzi and require positive results on two of three tests, including complement fixation, indirect immunofluorescence, passive agglutination or ELISA, to accurately detect T. cruzi infection. The cost and difficulty of such tests has prevented the screening of blood or sera in many endemic areas.

An improved method of detecting T. cruzi infection was disclosed in U.S. Pat. No. 5,304,371, which is incorporated herein by reference. In that patent, an antigenic epitope of T. cruzi was disclosed that detected antibodies to T. cruzi, and thus infection with the parasite, in most infected patients. However, while this method is an improvement over prior methods, the sensitivity of the technique is only about 93% (i.e., only about 93% of infections could be diagnosed).

Similar difficulties arise in the diagnosis of Leishmania infections. A variety of species of Leishmania infect humans, causing human diseases characterized by visceral, cutaneous, or mucosal lesions. Millions of cases of leishmaniasis exist worldwide, and at least 400,000 new cases of visceral leishmaniasis (VL) are diagnosed annually. Leishmania species are transmitted to humans and other mammals by the bite of a sand fly or through blood transfusions with contaminated blood.

VL is generally caused by L. donovani in Africa and India, L. infantium in Southern Europe, or L. chagasi in Latin America. In VL, high levels of parasite specific antibodies are observed prior to the detection of antigen specific T cell responses (Ghose et al., Clin. Exp. Immunol. 40:318–326, 1980). This antibody response has been used for serodiagnosis (commonly by immunofluorescence techniques) of infection with L. chagasi and L. donovani. Those serodiagnosis methods currently available for diagnosing VL typically use whole or lysed parasites. Such methods are prone to inaccuracy and cross-reaction with a variety of other diseases, and fail to detect some cases of the potentially fatal disease early enough to allow effective treatment.

Accordingly, there is a need in the art for more specific and sensitive methods of detecting T. cruzi and Leishmania infections in blood supplies and individuals. The present invention fulfills these needs and further provides other related advantages.

SUMMARY OF THE INVENTION

Briefly stated, this invention provides compounds and methods for detecting and protecting against T. cruzi infection in individuals and in blood supplies, and for screening for T. cruzi and Leishmania infections in biological samples. In one aspect, the present invention provides methods for detecting T. cruzi infection in a biological sample, comprising (a) contacting the biological sample with a first polypeptide comprising the amino acid sequence of SEQ ID NO: 11; and (b) detecting in the biological sample the presence of antibodies that bind to the polypeptide, thereby detecting T. cruzi infection in the biological sample.

In a related aspect, the present invention provides methods for detecting T. cruzi infection in a biological sample, comprising (a) contacting the biological sample with a first polypeptide comprising the amino acid sequence of SEQ ID NO: 11; (b) contacting the biological sample with a second polypeptide comprising an amino acid sequence selected from the group consisting SEQ ID NO: 8 and 9; and (c) detecting in the biological sample the presence of antibodies that bind to the first or second polypeptide, thereby detecting T. cruzi infection in the biological sample.

In yet another related aspect of this invention, methods for detecting T. cruzi infection in a biological sample are provided, comprising (a) contacting a biological sample with a polypeptide comprising the amino acid sequence of SEQ ID NO: 11, and further comprising at least one amino acid sequence selected from the group consisting of SEQ ID NO: 4, 8 and 9; and (b) detecting in the biological sample the presence of antibodies that bind to the polypeptide, thereby detecting T. cruzi infection in the biological sample.

In another aspect of the subject invention, polypeptides are provided comprising (a) the amino acid sequence of SEQ ID NO: 11; and (b) at least one amino acid sequence selected from the group consisting SEQ ID NO: 4, 8 and 9.

Within related aspects, DNA sequences encoding the above polypeptides, expression vectors comprising these DNA sequences and host cells transformed or transfected with such expression vectors are also provided.

In another aspect, diagnostic kits for detecting T. cruzi infection in a biological sample are provided, comprising (a) a first polypeptide comprising the amino acid sequence of SEQ ID NO: 11, and a second polypeptide comprising an amino acid sequence selected from the group consisting SEQ ID NO: 4, 8 and 9; and (b) a detection reagent.

Within related aspects, pharmaceutical compositions, comprising the above polypeptides and a physiologically acceptable carrier, and vaccines, comprising the above polypeptides and an adjuvant, are also provided.

In yet other aspects, methods for detecting T. cruzi infection in a biological sample are provided, comprising (a) contacting the biological sample with a monoclonal antibody that binds to a polypeptide comprising an amino acid sequence of SEQ ID NO: 11; and (b) detecting in the biological sample the presence of T. cruzi parasites that bind to the monoclonal antibody. Kits for use in such methods are also provided.

These and other aspects of the present invention will become apparent upon reference to the following detailed description and attached drawings.

BRIEF DESCRIPTION OF THE DRAWINGS

FIG. 1 shows the DNA sequence of the TcE cDNA(SEQ ID NO: 2).

FIG. 2 depicts the deduced amino acid sequence of the TcE cDNA (SEQ ID NO: 1), with the tandemly arrayed copies of the seven amino acid repeat unit underlined.

FIG. 3 shows the amino acid sequence of TcEr (SEQ ID NO: 3), a polypeptide that contains the three degenerate seven amino acid repeat units present in TcE.

FIG. 4 depicts the amino acid sequence of TcD (SEQ ID NO: 6), with the sequence of an antigenic TcD polypeptide underlined.

FIG. 5 shows the amino acid sequence of PEP2 (SEQ ID NO: 4).

DETAILED DESCRIPTION OF THE INVENTION

Figure 6:
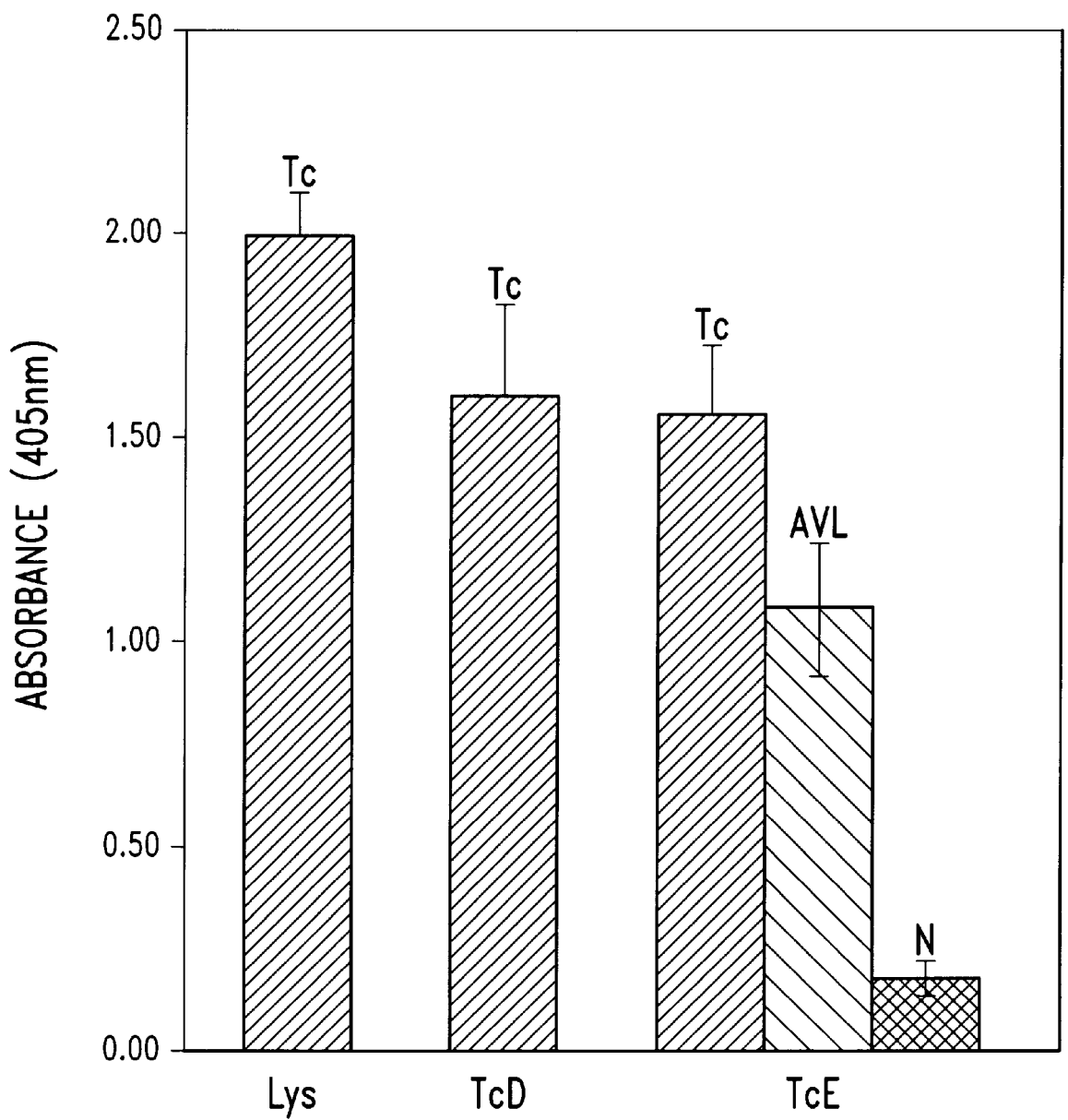
FIG. 6 illustrates the results of an ELISA comparing the reactivities of T. cruzi (Tc) infection sera with lysate (Lys), TcD, and TcE. The reactivities of sera from visceral Leishmaniasis patients (AVL) and uninfected normal (N) sera with TcE is also shown.

As noted above, the present invention is generally directed to compounds and methods for detecting and protecting against T. cruzi infection in individuals and in blood supplies. The compounds of this invention generally comprise one or more antigenic epitopes of T. cruzi proteins. In particular, polypeptides comprising an antigenic epitope of a 35 kD T. cruzi homolog to the eukaryotic ribosomal protein L19E are disclosed. The sequence of the 35 kD T. Cruzi homolog (referred to herein as TcE) is set forth in FIG. 2, as well as in SEQ ID NO: 1. As used herein, the term "polypeptide" encompasses amino acid chains of any length, wherein the amino acid residues are linked by covalent peptide bonds. The use of antigenic epitopes from additional T. cruzi proteins, in combination with an epitope of TcE, to enhance the sensitivity and specificity of the diagnosis is also disclosed.

The compounds and methods of this invention also encompass antigenic variants of the antigenic polypeptides. As used herein, an "antigenic variant" is a polypeptide that differs from the recited polypeptide only in conservative substitutions or modifications, such that it retains the antigenic properties of the recited polypeptide. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: ala, pro, gly, glu, asp, gin, asn, ser, thr; cys, ser, tyr, thr; val, ile, leu, met, ala, phe; lys, arg, his; and phe, tyr, trp, his. Preferred substitutions include changes among valine, threonine and alanine, and changes between serine and proline. Variants may also, or alternatively, contain other conservative modifications, including the deletion or addition of amino acids that have minimal influence on the antigenic properties, secondary structure and hydropathic nature of the polypeptide. For example, the polypeptide may be conjugated to a linker or other sequence for ease of synthesis or to enhance binding of the polypeptide to a solid support.

In one aspect of the invention, polypeptides comprising an antigenic epitope of the T. cruzi L19E homolog are provided. The 35 kD L19E homolog may be isolated by screening a T. cruzi expression library for clones that express antigens which possess the following properties: (1) strong reactivity with sera from T. cruzi-infected patients, (2) reactivity with sera from T. cruzi-infected patients whose infections cannot be detected using an antigenic epitope of the TcD antigen and (3) lack of reactivity with normal and heterologous patient sera (i.e., sera from patients with other pathologies, such as leishmaniasis, leprosy and tuberculosis). Accordingly, a T. cruzi amastigote cDNA expression library may be first screened with pooled sera from T. cruzi-infected individuals. Clones that express proteins which react with the pooled sera may then be subjected to a second screen using sera from T. cruzi-infected individuals whose infection cannot be detected with antigenic polypeptides derived from an antigenic epitope of the T. cruzi TcD antigen. Finally, clones that express proteins which react with the sera in the first two screens may be subjected to a third screen using normal or heterologous patient sera.

All of the above screens may be generally performed using methods known to those of ordinary skill in the art or as described in Sambrook et al., *Molecular Cloning: A*

*Laboratory Manual*, Cold Spring Harbor Laboratories, Cold Spring Harbor, N.Y. 1989, which is incorporated herein by reference. Briefly, the bacteriophage library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents for screening purposes contain a "binding agent," such as Protein A, Protein G, IgG or a lectin, coupled to a reporter group. Preferred reporter groups include, but are not limited to, enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing cDNAs that express a protein that binds to an antibody in the serum may be isolated and purified by techniques known to those of ordinary skill in the art. Appropriate methods may be found, for example, in Sambrook et al., *Molecular Cloniing: A Laboratory Manual*.

A cDNA encoding the *T. cruzi* L19E homolog (i.e., TcE) that was isolated using the above screens is shown in FIG. 1, and the deduced amino acid sequence of the TcE cDNA is shown in FIG. 2. The N-terminal portion of TcE (the region not underlined in FIG. 2) is homologous to the eukaryotic ribosomal protein L 19E. Following the region of L19E homology are sixteen copies of a tandemly arrayed seven amino acid repeat, which are underlined in FIG. 2.

Antigenic regions of TcE may generally be determined by generating polypeptides containing portions of the TcE sequence and evaluating the reactivity of the polypeptides with sera from *T. cruzi*-infected individuals using, for example, an enzyme linked immunosorbent assay (ELISA). Suitable assays for evaluating reactivity with *T. cruzi*-infected sera are described in more detail below. Portions of TcE containing at least 7 amino acids from the tandem repeat region (i.e., residues 137–247 in FIG. 2) have generally been found to be antigenic. Accordingly, polypeptides comprising at least a 7 amino acid portion of the sequence between residues 137 and 247 of TcE, and antigenic variants thereof, are within the scope of this invention. Preferably, the antigenic polypeptides contain at least a 14 amino acid portion, and more preferably at least a 21 amino acid portion, of the TcE sequence between residues 137 and 247. In certain embodiments, the N-terminal region of TcE that is homologous to L19E (i.e., residues 1–136) is substantially excluded from the antigenic polypeptide to avoid cross-reactivity with anti-Leishmania antibodies. In these embodiments, the polypeptide generally contains no more than about 5 consecutive amino acids from the N-terminal region. In one specific embodiment, the antigenic polypeptide is TcEr, a 21 amino acid peptide that comprises three degenerate 7 amino acid repeat units. The sequence of TcEr is provided in FIG. 3. Most preferably, the antigenic polypeptide comprises the TcE variant TcE(3A) (SEQ ID NO: 11).

In a related aspect, combination polypeptides comprising antigenic epitopes of multiple *T. cruzi* peptides are disclosed. A "combination polypeptide" is a polypeptide in which antigenic epitopes of different *T. cruzi* peptides, or antigenic variants thereof, are joined though a peptide linkage into a single amino acid chain. The epitopes may be joined directly (i.e., with no intervening amino acids) or may be joined by way of a linker sequence (e.g., Gly-Cys-Gly) that does not significantly alter the antigenic properties of the epitopes.

In preferred embodiments, the combination polypeptide comprises an antigenic TcE epitope along with an antigenic epitope derived from the *T. cruzi* TcD antigen (disclosed in U.S. Pat. No. 5,304,371) and/or the PEP2 antigenic epitope (discussed, for example, in Peralta et al., *J. Clin. Microbiol.* 32:971–74, 1994). Preferred TcE epitopes for use in combination peptides are as described above. The TcD antigenic epitope preferably has the amino acid sequence Ala Glu Pro Lys Ser Ala Glu Pro Lys Pro Ala Glu Pro Lys Ser (SEQ ID NO: 8) or the amino acid sequence Ala Glu Pro Lys Pro Ala Glu Pro Lys Ser Ala Glu Pro Lys Pro (SEQ ID NO: 9), and the PEP2 epitope preferably has the amino acid sequence Gly Asp Lys Pro Ser Pro Phe Gly Gln Ala Ala Ala Gly Asp Lys Pro Ser Pro Phe Gly Gln Ala (SEQ ID NO: 4; provided in FIG. 5). Combination polypeptides of this invention may also contain a TcD antigenic epitope in combination with PEP2, with or without an antigenic epitope of TcE. It has been found that location of the TcE epitope at one end of the combination polypeptide provides superior binding to a solid support. Accordingly, for polypeptides that contain a TcE epitope, that epitope is preferably located at either the N-terminal or the C-terminal end of the combination polypeptide.

The polypeptides of this invention may be generated using techniques well known to those of ordinary skill in the art. Polypeptides having fewer than about 100 amino acids, and generally fewer than about 50 amino acids, can be synthesized using, for example, the Merrifield solid-phase synthesis method, where amino acids are sequentially added to a growing amino acid chain. See Merrifield, *J Am. Chem. Soc.* 85:2149–2146, 1963. Equipment for automated synthesis of polypeptides is commercially available from suppliers such as Perkin Elmer/Applied Biosystems Division, Foster City, Calif. Thus, for example, the 22 amino acid PEP2 polypeptide, or portions thereof, may be synthesized by this method. Similarly, antigenic epitopes of TcE or TcD, which preferably contain 1 to 3 repeat units of those proteins, may be prepared using an automated synthesizer.

Alternatively, the polypeptides of this invention may be prepared by expression of recombinant DNA encoding the polypeptide in cultured host cells. Preferably, the host cells are *E. coli*, yeast, an insect cell line (such as Spodoptera or Trichoplusia) or a mammalian cell line, including (but not limited to) CHO, COS and NS-1. The DNA sequences expressed in this manner may encode naturally occurring proteins, such as TcE and TcD, portions of naturally occurring proteins, or antigenic variants of such proteins. Expressed polypeptides of this invention are generally isolated in substantially pure form. Preferably, the polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

In another aspect of this invention, methods for detecting *T. cruzi* infection in individuals and blood supplies are disclosed. In general, *T. cruzi* infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, *T. cruzi* infection may be detected using any of the polypeptides or combination polypeptides discussed above, or antigenic variants thereof More specifically, the polypeptide or polypeptides are used to determine the presence or absence of antibodies to the polypeptide or polypeptides in the sample, relative to a predetermined cut-off value.

There are a variety of assay formats known to those of ordinary skill in the art for using purified antigen to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen. Nitrocellulose will bind approximately 100 $\mu$g of protein per cm$^3$.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook (1991) at A12–A13; Jerry March, *Advanced Organic Chemistry* (2d. ed. 1977) at 820–823).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20™ (Sigma Chemical Co.). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detect the presence of *T. Cruzi* antibody within a *T. cruzi*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *T. cruzi* antibodies in the sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the predetermined cut-off value is considered positive for T. cruzi antibodies and T. cruzi infection.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of T. cruzi antibodies in the sample. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In one embodiment of the assays discussed above, the antibodies are detected using a polypeptide comprising at least a 7 amino acid portion, preferably a 14 amino acid portion, and more preferably at least a 21 amino acid portion, of the sequence between residues 137 and 247 of TcE, or an antigenic variant thereof In general, the N-terminal region of TcE that is homologous to L19E (i.e., residues 1–136) is substantially excluded from the antigenic polypeptide to avoid cross-reactivity with anti-Leishmania antibodies. Most preferably, the antigenic polypeptide is TcEr.

In additional embodiments, methods for enhancing the sensitivity of the assays described above are disclosed. In general, the sensitivity may be significantly improved by using one or more additional T. cruzi antigens in combination with the TcE epitope. In particular, antigenic epitopes from TcD and/or PEP2 (or antigenic variants thereof), which are provided above, may be mixed with the TcE polypeptide. Alternatively, a TcD antigenic epitope may be combined with PEP2, in the absence of TcE antigen.

These assays may be performed using sets of distinct polypeptides. In one two-polypeptide embodiment, one of the polypeptides contains an antigenic epitope of TcE and the other contains an antigenic epitope of TcD. In another such embodiment, one of the polypeptides contains an antigenic epitope of TcE and the other contains PEP2 or an antigenic portion thereof In a third such embodiment, one of the polypeptides contains a PEP2 antigenic epitope and the other contains an epitope of TcD. The assays may also be performed using three polypeptides, one containing a TcE epitope, one containing a TcD epitope and a third containing a PEP2 epitope.

Preferably, the antigenic polypeptides are immobilized by adsorption on a solid support such as a well of a microtiter plate or a membrane, as described above, such that a roughly similar amount of each polypeptide contacts the support, and such that the total amount of polypeptide in contact with the support ranges from about 10 ng to about 100 µg. The remainder of the steps may generally be performed as described above.

In an alternative embodiment, combination polypeptides are employed. As discussed above, a combination polypeptide is a polypeptide in which antigenic epitopes of different T. Cruzi peptides are joined though one or more peptide linkages into a single amino acid chain. Any of the above antigenic epitopes, or antigenic variants thereof, may be incorporated into a combination polypeptide. Thus, a combination polypeptide could contain a TcE epitope linked to a TcD epitope; a TcE epitope linked to PEP2; a TcD epitope linked to PEP2; or a TcE epitope, a TcD epitope and PEP2 linked together within the same polypeptide.

In another aspect of this invention, methods are provided for screening a biological sample for T. cruzi and/or Leishmania species. In these methods, the biological sample is analyzed for antibodies to TcE, or certain portions thereof In general, the assays may be performed as described above, except that the polypeptide employed comprises amino acids 1 to 143 of TcE, as represented in FIG. 2. The N-terminal portion of this antigen (amino acids 1–136) has been found to react with antibodies to Leishmania. Any species of Leishmania may be detected using this sequence, including L. major, L. tropica, L. chagasi, L. donovani, L. infantum, L. guyanesis, L. braziliensis, L. amazonensis and L. panamensis. The inclusion of amino acid sequence from the tandem repeat portion of TcE results in the detection of antibodies specific for T. cruzi as well. Additional amino acids from the portion of TcE between amino acid 145 and the carboxy terminus may also be included. In a preferred embodiment, the antigen employed in the screen for both T. cruzi and Leishmania is the full length TcE protein, shown in FIG. 2. Antigenic variants of TcE, or a portion thereof comprising at least amino acids 1–136 and a repeat unit, may also be employed.

Following the above screen for T. cruzi and/or Leishmania, the parasite may be identified using methods specific for either T. cruzi or Leishmania. For example, any of the methods described above may be employed to detect the presence of T. cruzi in the sample. Any of the methods known to those in the art may be employed to detect Leishmania.

In yet another aspect of this invention, methods are provided for detecting T. cruzi in a biological sample using monospecific antibodies (which may be polyclonal or monoclonal) to polypeptides comprising epitopes of one or more of TcE, TcD and PEP2. Preferred epitopes are those recited above, and antigenic variants thereof Antibodies to these purified or synthesized polypeptides may be prepared by any of a variety of techniques known to those of ordinary skill in the art. See, e.g., Harlow and Land, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Monospecific antibodies to polypeptides comprising epitopes of one or more of TcE, TcD and PEP2 may be used to detect *T. cruzi* infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of *T. cruzi* in the sample. Any of the reporter groups discussed above in the context of ELISAs may be used to label the monospecific antibodies, and binding may be detected by any of a variety of techniques appropriate for the reporter group employed. Other formats for using monospecific antibodies to detect *T. cruzi* in a sample will be apparent to those of ordinary skill in the art, and the above formats are provided solely for exemplary purposes.

In another aspect of this invention, vaccines and pharmaceutical compositions are provided for the prevention of *T. cruzi* infection, and complications thereof, in a mammal. The pharmaceutical compositions generally comprise one or more polypeptides, containing one or more antigenic epitopes of *T. cruzi* proteins, and a physiologically acceptable carrier. The vaccines comprise one or more of the above polypeptides and an adjuvant, for enhancement of the immune response.

Routes and frequency of administration and polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2–6 week period. Preferably, two doses are administered, with the second dose 2–4 weeks later than the first. A suitable dose is an amount of polypeptide that is effective to raise antibodies in a treated mammal that are sufficient to protect the mammal from *T. cruzi* infection for a period of time. In general, the amount of polypeptide present in a dose ranges from about 1 pg to about 100 mg per kg of host, typically from about 10 pg to about 1 mg, and preferably from about 100 pg to about 1 $\mu$g. Suitable dose sizes will vary with the size of the animal, but will typically range from about 0.01 mL to about 5 mL for 10–60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, *Bordella pertussis* or *Mycohacterium tuherculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The following Examples are offered by way of illustration and not by way of limitation.

EXAMPLES

Example 1

Preparation of TcE

This Example illustrates the isolation of a cDNA encoding TcE and the preparation of TcE using the cDNA.

Total RNA was isolated from the amastigote stage of the *T. cruzi* strain MHOM/CH/00/Tulahuen using the acid guanidium isothiocyanate method. An unamplified cDNA expression library was prepared from this RNA using the ZAP-cDNA unidirectional cloning kit (Stratagene, Inc., La Jolla, Calif.). Briefly, the first cDNA was constructed using an oligo dT primer with Xho I adapters. Following synthesis of the second strand, Eco RI adapters were added and the double-stranded cDNA was digested with Xho I and ligated into the unizap phage lambda predigested with Eco RI and Xho I.

For immunoscreening of a library, serum samples from five *T. cruzi*-infected individuals were pooled. Anti-*E. coli* reactivity was removed from the serum prior to screening by adsorption. 60,000 pfu of the unamplified library was screened with the serum pool and plaques expressing proteins that reacted with the serum were detected using protein A-horseradish peroxidase (with the ABTS substrate) and isolated. Excision of the pBSK(−) phagemid (Stratagene, Inc., La Jolla, Calif.) was carried out according to the manufacturer's protocol. Overlapping clones were generated by exonuclease III digestion and single-stranded templates were isolated after infection with VCSM 13 helper phage. The DNA was sequenced by the dideoxy chain termination method or by the Taq di-terminator system, using an Applied Biosystem automated sequencer, Model 373A. Forty-two clones that expressed proteins which reacted with the sera were then isolated from this screen.

Of the isolated clones, 33 that reacted strongly or very strongly with the patient sera were purified and sequenced. Twelve of these clones (about 35%) were members of a highly immunogenic *T. cruzi* P protein family. One clone corresponded to a heat shock antigen gene. Two clones showed sequence identity to *T. cruzi* ubiquitin genes. The remaining 18 clones represented new *T. cruzi* genes. Six of these had sequence similarity with eukaryotic ribosomal proteins (L19E, S8 and S-phase specific) and 12 represented genes that were not homologous to sequences in the Gen-Bank.

The isolated clones were further screened by the above procedure using heterologous patient sera from Leishmania-infected individuals. The members of the P protein family showed cross reactivity with the heterologous sera, and were not pursued further. The remaining clones were then screened with sera from individuals that were infected with *T. cruzi*, but whose infections could not be detected using the antigenic epitopes of TcD. The clones that had sequence similarity with eukaryotic ribosomal proteins were strongly reactive with the TcD negative sera. Of these clones, the L19E homolog was unique in that its homology to the eukaryotic ribosomal protein was confined to the N-terminal portion of the protein. This homolog (TcE) was exceptionally reactive with the test serum. The sequence of the cDNA encoding TcE is shown in FIG. 1, and the predicted amino acid sequence is provided in FIG. 2.

Full length TcE was produced and purified from *E coli* transformed with an expression vector containing the cDNA insert encoding TcE. A transformed bacterial colony was used to inoculate 20 ml of LB-broth and grown at 37° C. overnight. A 500 ml culture was then inoculated with the uninduced overnight culture at a 50:1 dilution. This culture was grown at 37° C. until the A560 was approximately 0.4 to 0.5. IPTG was then added to a final concentration of 2 mM and the culture was allowed to grow for 4 hours. The cells were harvested by centrifugation, lysed, and fractionated into a pellet and soluble components. TcE which remained in the soluble supernatant was fractionated by sequential ammonium sulfate precipitations. Purification to homogeneity was accomplished by preparative SDS-PAGE electrophoresis, followed by excision and electroelution of the recombinant antigen.

Example 2

Preparation of TcEr

This Example illustrates the preparation of a polypeptide that comprises an antigenic epitope of TcE. While the minimum sequence representing the antigenic epitope of TcE is one 7 amino acid repeat, a peptide sequence having three degenerate repeats was selected for study in order to maximize reactivity. The TcEr polypeptide was synthesized on an ABI 430A peptide synthesizer using FMOC chemistry with HPTU (O-Benzotriazole-N,N,N',N'-tetramethyluronium hexafluorophosphate) activation. A Gly-Cys-Gly sequence was attached to the amino terminus of the peptide to provide a method of conjugation or labeling of the peptide. Cleavage of the peptides from the solid support was carried out using the following cleavage mixture: trifluoroacetic acid:ethanedithiol:thioanisole::water:phenol (40:1:2:2:3). After cleaving for 2 hours, the peptides were precipitated in cold methyl-t-butyl-ether. The peptide pellets were then dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) was used to elute the peptides. Following lyophilization of the pure fractions, the peptides were characterized using electrospray mass spectrometry and by amino acid analysis. The synthesized peptide (TcEr) has the sequence shown in FIG. 3.

Example 3

Detection of *T. cruzi* Infection In Serum

This Example illustrates the detection of *T. cruzi* infection using the compounds and methods of this invention. The assays described below were performed in ELISA format.

A. TcE

TcE antigen was purified from induced *E. coli* extracts as described above for serological evaluation of patient sera by ELISA. The ELISA assay was performed as follows. Microtiter plates were coated overnight at 4° C. with 25 ng per well of recombinant TcE in 50 μl of coating buffer. After washing with PBS/0.1% Tween™ 20 (PBS-T), 50 μl of sera (diluted 1:100) were added and incubated for 30 minutes at room temperature. An additional wash step was performed with PBS-T. Protein A-horseradish peroxidase conjugate was diluted 1:10,000 in PBS-T, and 50 μl of the diluted conjugate was added to each well and incubated for 30 minutes at room temperature. The wash step with PBS-T was again repeated, and 100 μl of substrate (ABTS/$H_2O_2$, Zymed Kit, Catalog No. 00-2011) was added per well and incubated for 30 minutes at room temperature under low light. The colorimetric reaction was terminated with 100 μl of 5% sodium dodecyl sulfate (SDS) and absorbance was read at 405 nm.

Of 36 *T. cruzi* infection sera that were initially tested, 35 (97.2%) tested positive using TcE, with absorbance values ranging from 0.25 to greater than 2.0. The average absorbance value is shown in FIG. 6, which also compares the reactivity of TcE with that of TcD and lysate. Of particular importance, all 8 patient sera that were either negative or had low antibody titers to TcD reacted relatively strongly with TcE. These results are shown in Table 1 below.

TABLE 1

Reactivities of TcD-Negative Sera with TcE

| Patient No. | Absorbance (405 nm) | |
| --- | --- | --- |
| | TcD | TcE |
| 3 | 0.06 | 0.61 |
| 23 | 0.00 | 1.99 |
| 53 | 0.00 | 0.61 |
| 165 | 0.00 | 0.91 |
| 170 | 0.00 | 0.18 |
| c4 | 0.02 | 2.50 |
| ch14 | 0.03 | 0.41 |
| 452 | 0.03 | 0.76 |

It was also found that some patient sera that had low absorbance values with TcE were reactive with TcD. TcE therefore has the ability to complement TcD, thereby increasing diagnostic sensitivity.

The specificity of TcE was further evaluated using sera from Leishmania-infected individuals, as well as normal sera. Cross-reactivity with sera from Leishmania-infected individuals (AVL) was observed, as shown in FIG. 6. Accordingly, the full-length TcE antigen may be used to screen patients for the presence of either T. cruzi or Leishmania infection. Following a positive result using TcE, however, additional tests specific for either T. cruzi or Leishmania will need to be performed in order to distinguish between the two parasites.

B. TcEr

Figure 7:
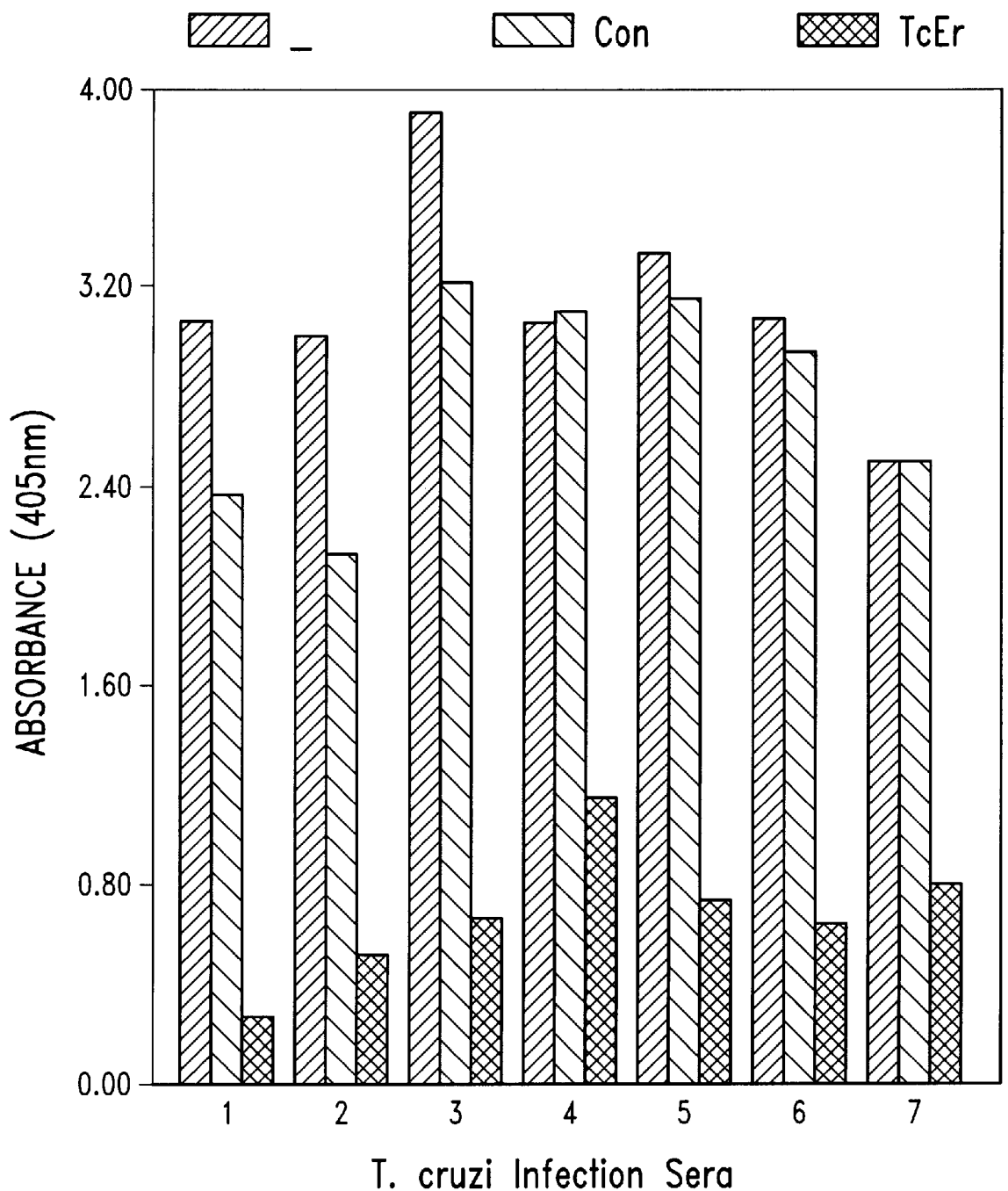
FIG. 7 illustrates the results of a competition ELISA of T. cruzi infection sera on TcE in the absence (−) or presence of 5 μg of synthetic control (CON) or the TcEr peptide.

To evaluate the reactivity of TcEr, the peptide was used in an inhibition study, where its ability to compete for the binding of T. cruzi-infected sera to TcE was measured. A competition ELISA was performed as follows. Microtiter plates were coated overnight at 4° C. with 25 ng per well of recombinant TcE in 50 $\mu$l of coating buffer. After washing with PBS-T, 50 $\mu$l of serum obtained from a T. cruzi-infected individual (diluted 1:100 and preincubated with 5 $\mu$g of peptide for 1 hour at room temperature) was added and incubated for 30 minutes at room temperature. Bound antibody was detected using protein A-horseradish peroxidase with ABTS substrate and the absorbance was measured at 405 nm. Of seven individual T. cruzi-infected sera tested, TcEr was efficient at competing the binding of sera on TcE with inhibition values ranging from 62%–90%. A control peptide with amino acid residues derived from the non-coding reading frame of TcE had minimal effect in the same competition assay. These results are depicted in FIG. 7. Accordingly, TcEr represents the immuno-dominant B cell epitope of TcE.

Figure 8:
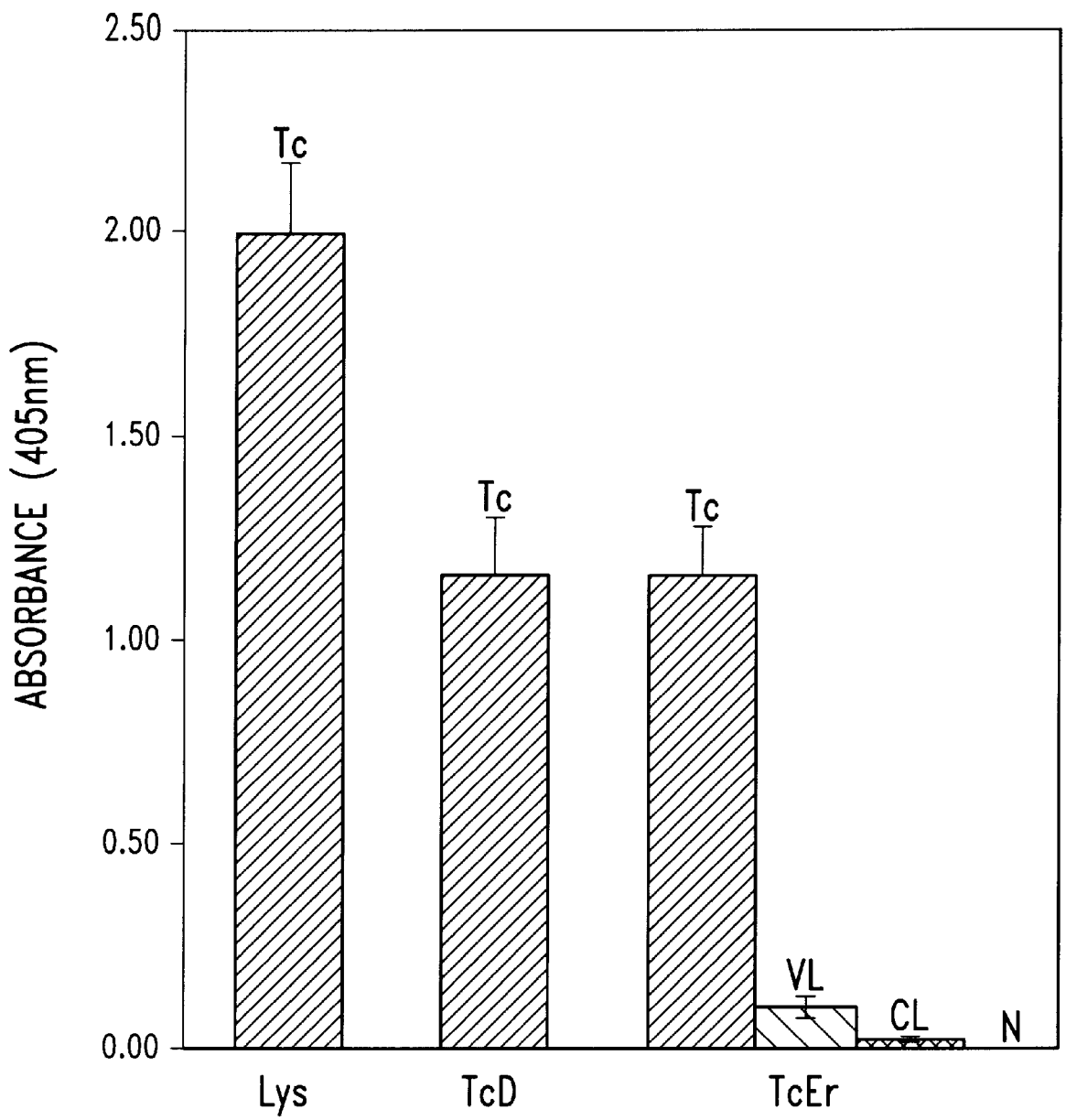
FIG. 8 illustrates the results of an ELISA evaluating the reactivities of T. cruzi (Tc) infection sera on lysate (Lys), TcD, and TcEr. The reactivities of sera from visceral Leishmaniasis patients (AVL), cutaneous Leishmaniasis (CL), and uninfected normal (N) control sera on TcEr are also shown.

The specificity of TcEr reactivity was also evaluated, along with the sero-reactivity compared to lysate and TcD. In these experiments, ELISAs were performed in which microtiter plates were coated overnight at 4° C. with 100 ng per well of T. cruzi lysate, 250 ng per well of recombinant TcD peptide (i.e., the polypeptide having the 15 amino acid sequence underlined in FIG. 4, with a Gly-Cys-Gly sequence attached to the amino terminus) or 25 ng per well of synthetic TcEr peptide in 50 $\mu$l of coating buffer. After washing with PBS-T, 50 $\mu$l of serum from a T. cruzi-infected individual (diluted 1:100) was added and incubated for 30 minutes at room temperature. Bound antibody was detected using the protein A-horseradish peroxidase and the absorbance was measured at 405 nm. The results from this experiment are depicted in FIG. 8. Using three standard deviations above the average mean of normal sera as a criteria for scoring patient sera as positive, 66 of 69 (95.6%) T. cruzi infected serum samples were positive when tested with TcEr, and had an average absorbance value of 1.16.

FIG. 8 also shows the reactivity of TcEr with sera from visceral leishmaniasis patients (AVL), cutaneous leishmaniasis (CL), and uninfected normal (N) control sera. All 16 AVL infection sera which were positive on the full-length TcE antigen were negative when the assay was performed with TcEr. Therefore, the cross-reactivity of the heterologous Leishmania infection sera with TcE was directed against the non-repeat L19E homology domain. We also tested the reactivities of patient sera from individuals with cutaneous leishmaniasis (CL) with TcEr. All 39 CL patient sera were negative when the assay was performed with TcEr. These results indicate that TcEr is as reactive as TcD with sera from T. cruzi-infected individuals, and that TcEr is highly specific for the detection of T. cruzi. Therefore, TcEr has satisfied the requirements as a sensitive and specific diagnostic antigen for T. cruzi infection.

C. Multiple Antigenic Polypeptides

To enhance the sensitivity of the assays described above, the assays were repeated using multiple polypeptides, each of which contained an epitope from a different T. cruzi antigen. In particular, the TcD and TcE polypeptides were combined, as were the TcD and PEP2 polypeptides. The PEP2 polypeptide in all of these experiments consisted of the 22 amino acid sequence shown in FIG. 5, with a Gly-Cys-Gly sequence attached to the amino terminus, and the TcD peptide was as described above. The reactivity of these combinations was evaluated using the ELISA format, and was compared to the reactivities of each of the polypeptides individually.

The ELISA assays were performed as follows. Plastic 96-well plates (Corning Easy Wash High Binding, Corning Laboratories, Corning, N.Y.) were coated with 50 $\mu$l of the peptide or mixture of peptides. The TcD peptide employed in these assays has the sequence Ala Glu Pro Lys Ser Ala Glu Pro Lys Pro Ala Glu Pro Lys Ser (SEQ ID NO: 8), and was present in the 50 $\mu$l at a concentration of 10 $\mu$g/ml. The PEP2 sequence was the 22 amino acid sequence shown in FIG. 5, and this peptide was present in the 50 $\mu$l at a concentration of 2.5 $\mu$g/ml. The TcEr polypeptide had the sequence shown in FIG. 3, and 25 ng was present in the 50 $\mu$l. The peptides were diluted in 0.05 M carbonate buffer (pH 9.6). Plates were incubated for 1 hour at 37° C. and maintained at 4° C. until use for up to 1 month. For use, sensitized wells were washed with 0.01 M phosphate buffered saline (pH 7.2) containing 0.3% Tween 20 (PBS/T). Positive control, negative control, and unknown serum samples were diluted 1:20 in PBS/T containing 0.5% bovine serum albumin, and 50 $\mu$l was added to each well. After 30 minutes of incubation at room temperature, wells were washed six times with PBS/T. Fifty $\mu$l of protein-A peroxidase (Zymed Laboratories, San Francisco, Calif.), diluted in PBS/T-bovine serum albumin was added and the plates were incubated as described above. Wells were washed eight times with PBS/T and 100 $\mu$l of 2,2'-azino-di-3-ethylbenzethiazoline sulfonic acid (ABTS) substrate solution (50 $\mu$l of 50 X ABTS, 50 $\mu$l of 1.5% $H_2O_2$, 2.5 ml of 0.1 M citrate buffer (pH 4.1), Zymed Laboratories, San Francisco, Calif.) was added. After 15 minutes at room temperature, the enzymatic reaction was stopped by adding 100 $\mu$l of 10% sodium dodecylsulfate. $A_{405}$ values were determined with an ELISA reader (Titertek Multiskan, Flow Laboratories, McLean, Va.). For each test, 5 negative control serum samples and 2 positive Chagas' patient serum samples were included. Test results were considered acceptable only when negative control sera had absorbance values above 0.2 and positive control sera had absorbances between 0.6 and 0.8 (low positive), or between 1.2 and 1.4 (high positive). The cut off was determined for each test by calculating the mean of negative sera plus three standard deviations.

In an initial experiment, sera from 260 individuals living in an area of endemicity for Chagas' disease were assayed for *T. cruzi* infections described above. One hundred seventy-nine positive serum samples and 81 negative serum samples, characterized according to clinical findings and conventional serological tests (indirect immunofluorescent assay, indirect hemagglutination, and ELISA) were assayed. In this assay, the TcD peptide was found to be 93% sensitive and the PEP2 peptide was 91% sensitive. However, only 1 positive serum sample did not react with either peptide. These results are shown in Table 2 below.

TABLE 2

Reactivity of Serum Samples with TcD and PEP2 Peptides

| | No. of Samples | | | | | |
|---|---|---|---|---|---|---|
| | TcD | | PEP2 | | TcD/PEP2 | |
| Serum | Positive | Negative | Positive | Negative | Positive | Negative |
| Positive (n = 179) | 168 | 11 | 164 | 15 | 178 | 1 |
| Negative (n = 81) | 2 | 79 | 1 | 80 | 2 | 79 |

Accordingly, the ELISA test that employed a mixture of PEP2 and the TcD peptide had a sensitivity of greater than 99%.

The specificity of the TcD/PEP2 test was evaluated using sera from individuals living in an area of endemicity for Chagas' disease who had negative *T. cruzi* serology, as well as sera from patients with other pathologies. In these samples, 2 of 81 assays were positive, but no false-positive results were found among the 37 serum samples from individuals with other pathologies. The other pathologies represented in this study were cutaneous leishmaniasis, visceral leishmaniasis, leprosy, and tuberculosis. All cutaneous and visceral leishmaniasis serum samples were negative in the mixed peptide assay.

In a similar experiment, the reactivity of TcEr, alone and in combination with the TcD peptide, was evaluated and compared to the reactivity of *T. cruzi* lysate, the TcD peptide, PEP2, and the TcD/PEP2 mixture. Sixty-nine serum samples obtained from individuals with chronic Chagas' disease were assayed as described above using each of the above antigens. For comparison, similar assays were performed using 16 serum samples from individuals with acute visceral leishmaniasis and 33 serum samples from uninfected individuals The average mean absorbance for the infected and uninfected samples was determined for each of the different antigens, and is shown in Table 3, below, along with the standard deviation.

TABLE 3

Absorbances at 405 nm for Human Sera with *T. cruzi* Peptides and Parasite Lysate

| | A405 | | | | | |
|---|---|---|---|---|---|---|
| | Lysate | TcD | PEP2 | TcE | TcD/PEP2 | TcD/TcE |
| Chronic Chagas' (n = 69) | 2.000 ± 0.888 | 1.161 ± 1.220 | 1.163 ± 1.032 | 1.344 ± 1.050 | 1.443 ± 1.069 | 1.107 ± 0.987 |
| AVL (n = 16) | 0.488 ± 0.270 | 0.177 ± 0.165 | 0.099 ± 0.106 | 0.196 ± 0.139 | 0.246 ± 0.141 | 0.114 ± 0.105 |
| Normal (n = 33) | 0.032 ± 0.066 | 0.011 ± 0.020 | 0.003 ± 0.008 | 0.008 ± 0.022 | 0.006 ± 0.016 | 0.0003 ± 0.0017 |

Accordingly, the mixtures containing the TcD polypeptide and either PEP2 or TcEr were more sensitive and specific in these assays than any of the individual peptides. This was due to the fact that these polypeptides display complementary reactivities. As shown in Table 4, below, many of the patient sera that were either negative or had low antibody titers to TcD reacted relatively strongly with PEP2 and/or TcE.

TABLE 4

Reactivity of Serum Samples with *T. cruzi* Antigens

| | Absorbance (405 nm) | | |
|---|---|---|---|
| Patient No. | TcD | PEP2 | TcE |
| c4 | 0.067 | 0.598 | 2.245 |
| 53 | 0.015 | 0.494 | 0.146 |
| 40 | 0.016 | 0.105 | 0.895 |
| 56 | 0.001 | 0.184 | 0.088 |
| 76 | 0.027 | 0.920 | 0.695 |
| 139458 | 0.26 | 1.95 | 1.63 |
| ch14 | 0.10 | 1.25 | 0.07 |
| 103 | 0.40 | 1.33 | 0.30 |

These results demonstrate that combinations of PEP2 and/or TcE significantly enhance the sensitivity of the assay beyond that obtained with TcD alone.

In the third experiment, TcD was mixed with PEP2 or a fragment of PEP2. Specifically, the fragments of PEP2 containing residues 2 through 12 or residues 2 through 15 were employed. In each case, the portions of PEP2 were reactive, either alone or when mixed with TcD, but the 22 amino acid PEP2 sequence demonstrated superior reactivity. Thus, mixtures employing the 22 amino acid PEP2 sequence are more sensitive for *T. cruzi* infection than mixtures using the shorter sequences.

D. Combination Polypeptides

The experiments described above were repeated using combination polypeptides. First, sera from 12 patients infected with *T. cruzi* was assayed using combination polypeptide D/2, which consisted of the TcD peptide linked to the PEP2 sequence by way of the Gly-Cys-Gly linker. In addition, sera from 15 *T. cruzi*-negative individuals was assayed with the combination polypeptide D/2. In this experiment, the absorbance was measured at 450 nm because the substrate was tetramethylbenzidine (TMB), rather than ABTS. All of the 12 assays of sera from *T. cruzi*-infected individuals were positive (100%), and none of the sera from *T. cruzi*-negative individuals produced a positive result. Accordingly, the D/2 polypeptide is highly specific and sensitive for *T. cruzi* infection.

In another experiment, a combination polypeptide D/E, which contains the TcD peptide and the TcEr sequence, joined by the Gly-Cys-Gly linker, was evaluated alone and in combination with peptide D/2. Forty-four serum samples from *T. cruzi*-infected individuals were assayed, along with 24 samples from clinically normal individuals in the endemic regions of Brazil and 24 samples from clinically normal individuals in the United States. The results of each of the assays performed on the above serum samples are shown in Table 5 below.

TABLE 5

Reactivity of Serum Samples with Combination Polypeptides

| | No. of Samples | | | |
|---|---|---|---|---|
| | D/E | | D/E + D/2 | |
| Serum | Positive | Negative | Positive | Negative |
| Positive (n = 44) | 41 | 3 | 44 | 0 |
| Endemic Normal (n = 24) | 2 | 22 | 1 | 23 |
| U.S. Normal (n = 24) | 0 | 24 | 0 | 24 |

Accordingly, peptide D/E detected 41 of the 44 positive samples (93%) and the mixture of peptides D/E and D/2 detected all of the 44 positive serum samples (100%). Neither of the peptides produced a positive result in the assays of clinically normal serum samples from the United States. Since the "endemic normal" samples were only clinically normal (i.e., serodiagnostic assays had been performed), the positive result produced by the mixture of peptides D/E and D/2 may indicate an undiagnosed infection.

E. Tripeptide Mixture

The above assays were repeated using a mixture of the TcD peptide, TcEr, and PEP2. The 44 samples from *T. cruzi*-infected individuals, along with the 48 samples from clinically normal individuals (24 from the United States and 24 from endemic regions), which are described in Section D above, were assayed using a mixture of three separate polypeptides, each containing one of the above epitopes. In this experiment, all of the 44 *T. cruzi*-positive serum samples resulted in absorbances at 450 nm that were greater than three standard deviations above the average mean, and none of the normal serum samples from the United States yielded a positive result. Two of the negative samples from endemic regions of Brazil produced a positive result but, again, this may be the result of undiagnosed infections. Accordingly, the tripeptide mixture detected 100% of the positive serum samples, and showed a high specificity.

Example 4
Serological Reactivity of TcE Repeat Sequences

This example illustrates the diagnostic properties of several TcE repeat sequences.

The repeat sequence region of the recombinant TcEr contains several degeneracies resulting in residues where an A (alanine), T (threonine) or I (isoleucine) can be present in the repeat sequences. In order to represent all degeneracies, the original sequence of the synthetic TcE peptide was made with an A, T and I in a single peptide containing three repeats (see Example 2). In order to further map the repeat region and to determine the number of repeats required for serological activity, the following peptides were prepared as described in Example 2:

| original TcEr | KAAIAPAKAAAAPAKAATAPA | (SEQ ID NO: 10); |
|---|---|---|
| TcE(3A) | KAAAAPAKAAAAPAKAAAAPA | (SEQ ID NO: 11); |
| TcE(3T) | KAATAPAKAATAPAKAATAPA | (SEQ ID NO: 12); |
| TcE(3I) | KAAIAPAKAAIAPAKAAIAPA | (SEQ ID NO: 13); |
| TcE(2A) | KAAAAPAKAAAAPA | (SEQ ID NO: 14); |
| TcE(AT) | KAAAAPAKAATAPA | (SEQ ID NO: 15). |

Figure 9:
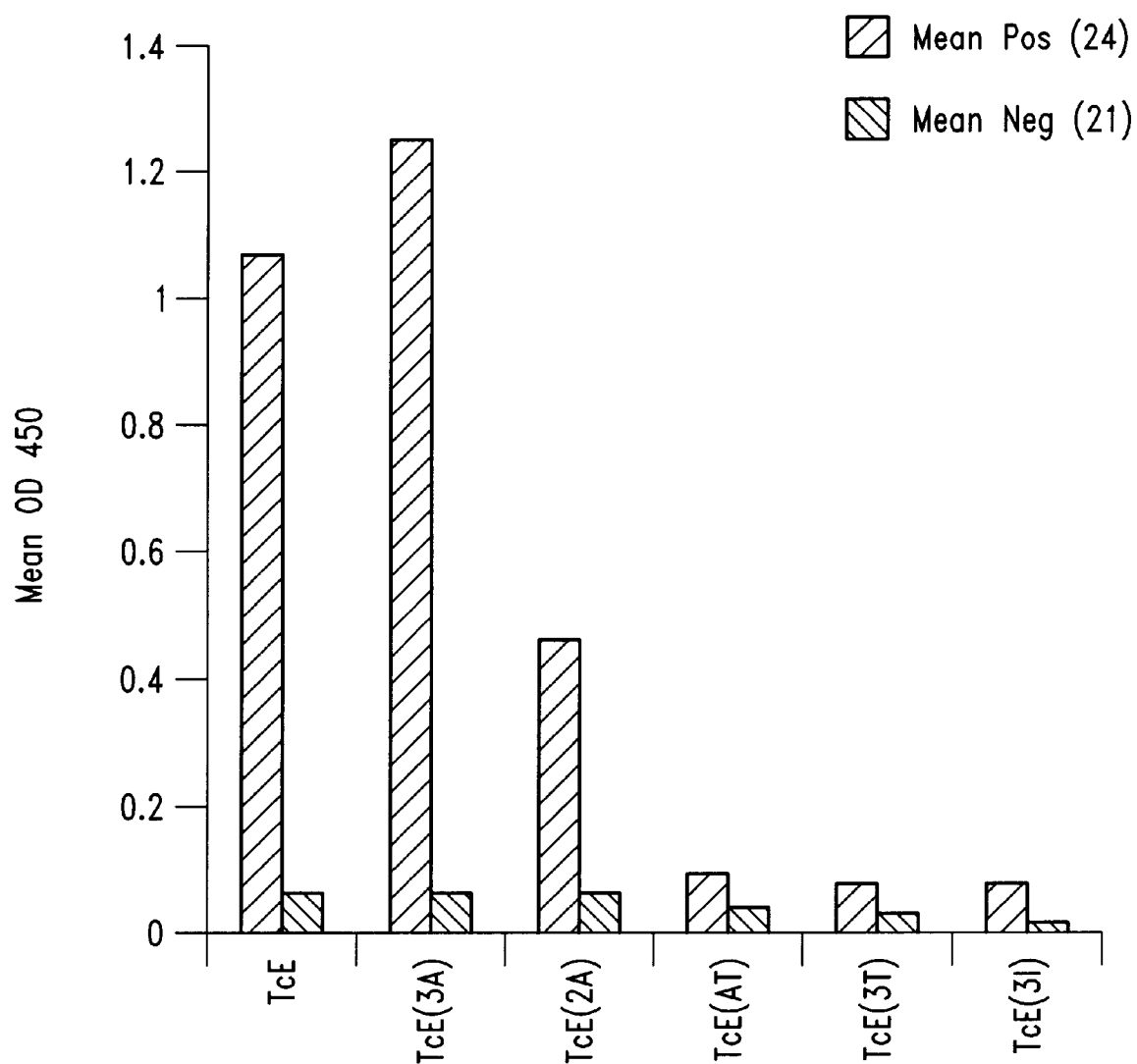
FIG. 9 illustrates the reactivities of TcE variants with T. cruzi-infected sera, as measured by ELISA.

The serological reactivity of these peptides was then compared. A total of 24 positive and 21 negative sera were tested with each of the TcE variants as the solid phase in an ELISA assay performed essentially as described in Example 3, using 25 ng/well of peptide and TMB as substrate. The reaction was stopped with 1N $H_2SO_4$ and read at 450 nm. The reactivity of the different peptides is shown in FIG. 9. The highest reactivity was seen with the 3-repeat peptide in which each repeat contained an A at the degenerate residue (TcE(3A)). This peptide displayed even higher reactivity than the original TcE sequence containing an A, T and I residue in the three repeats. The 3I and 3T variants, by contrast, were essentially negative with the *T. cruzi* positive samples tested. The sequence containing 2 repeats with A was clearly less reactive than the 3A sequence and the two repeat sequence with an A and a T was negative. Based on a cutoff of the mean of the negatives plus three standard deviations, the original TcE (A, T, I) detected 17 out of 24 positives and the 3A variant detected 19 out of 24 positives. It also appears that at least three repeats are required to obtain maximal serological activity.

From the foregoing, it will be appreciated that, although specific embodiments of the invention have been described herein for the purpose of illustration, various modifications may be made without deviating from the spirit and scope of the invention.

We claim:

1. A method for detecting *T. cruzi* infection in a biological sample, comprising:
   (a) contacting a biological sample with a first polypeptide comprising the amino acid sequence of SEQ ID NO: 11;
   (b) contacting the biological sample with a second polypeptide comprising an amino acid sequence selected from the group consisting of sequences recited in SEQ ID NO: 8 and 9; and
   (c) detecting in the biological sample the presence of antibodies that bind to at least one of the polypeptides, thereby detecting *T. cruzi* infection in a biological sample.

2. A method for detecting *T. cruzi* infection in a biological sample, comprising:
   (a) contacting the biological sample with a first polypeptide comprising a first amino acid sequence of SEQ ID NO: 11 and a second amino acid sequence selected from the group consisting of sequences recited in SEQ ID NO: 8 and 9; and
   (b) detecting in the biological sample the presence of antibodies that bind to the polypeptide, thereby detecting *T. cruzi* infection in the biological sample.

3. The method of claim 1, further comprising contacting the sample with a third polypeptide comprising an amino acid sequence recited in SEQ ID NO: 4.

4. The method of either of claims 1 or 2 wherein the first polypeptide further comprises an amino acid sequence recited in SEQ ID NO: 4.

5. The method of claim 1 wherein the biological sample is selected from the group consisting of blood, serum, plasma, saliva, cerebrospinal fluid and urine.

6. The method of claim 1 wherein the first polypeptide is bound to a solid support.

7. The method of claim 6, wherein the solid support comprises nitrocellulose, latex or a plastic material.

8. The method of claim 6 wherein the step of detecting comprises:

(a) removing unbound sample from the solid support;

(b) adding a detection reagent to the solid support; and (c) determining the level of detection reagent bound to the solid support, relative to a predetermined cutoff value, therefrom detecting *T. cruzi* infection in the biological sample.

9. The method of claim 8 wherein the detection reagent comprises a reporter group conjugated to a binding agent.

10. The method of claim 9, wherein the binding agent is selected from the group consisting of anti-immunoglobulins, Protein G, Protein A and lectins.

11. The method of claim 9 wherein the reporter group is selected from the group consisting of radioisotopes, fluorescent groups, luminescent groups, enzymes, biotin and dye particles.

12. A pharmaceutical composition comprising a polypeptide and a physiologically acceptable carrier, the polypeptide comprising the amino acid sequence of SEQ ID NO: 11 and at least one amino acid sequence selected from the group consisting of sequences recited in SEQ ID NO: 4, 8 and 9.

13. A diagnostic kit for detecting *T. cruzi* infection in a biological sample, comprising:

(a) a first polypeptide comprising the amino acid sequence of SEQ ID NO: 11; and (b) a detection reagent.

14. The kit of claim 13 further comprising a second polypeptide comprising an amino acid sequence selected from the group consisting of sequences recited in SEQ ID NO: 8 and 9.

15. The kit of either of claims 13 or 14 further comprising a third polypeptide comprising an amino acid sequence recited in SEQ ID NO: 4.

16. The kit of claim 13 wherein the first polypeptide further comprises at least one amino acid sequence selected from the group consisting of SEQ ID NO: 4, 8 and 9.

17. The kit of claim 13 wherein the detection reagent comprises a reporter group conjugated to a binding agent.

18. The kit of claim 17 wherein the binding agent is selected from the group consisting of anti-immunoglobulins Protein G, Protein A and lectins.

19. The kit of claim 17 wherein the reporter group is selected from the group consisting of radioisotopes, fluorescent groups, luminescent groups, enzymes, biotin and dye particles.

* * * * *